(12) United States Patent
McCord et al.

(10) Patent No.: US 9,809,794 B2
(45) Date of Patent: Nov. 7, 2017

(54) MATERIALS AND METHODS FOR ACHIEVING DIFFERENTIAL LYSIS OF MIXTURES WITH THE AID OF ALKALINE LYSIS AND PRESSURE CYCLING TECHNOLOGY (PCT)

(71) Applicant: The Florida International University Board of Trustees, Miami, FL (US)

(72) Inventors: Bruce R. McCord, Miami, FL (US); Deepthi V. Nori, Miami, FL (US); Nathan P. Lawrence, South Easton, MA (US); Richard Schumacher, South Easton, MA (US)

(73) Assignees: THE FLORIDA INTERNATIONAL UNIVERSITY BOARD OF TRUSTEES, Miami, FL (US); PRESSURE BIOSCIENCES, INC., South Easton, MA (US)

( * ) Notice: Subject to any disclaimer, the term of this patent is extended or adjusted under 35 U.S.C. 154(b) by 186 days.

(21) Appl. No.: 14/625,233

(22) Filed: Feb. 18, 2015

(65) Prior Publication Data
US 2015/0232917 A1 Aug. 20, 2015

Related U.S. Application Data

(60) Provisional application No. 61/941,201, filed on Feb. 18, 2014.

(51) Int. Cl.
*C12Q 1/68* (2006.01)
*C12N 1/06* (2006.01)
*C12N 15/10* (2006.01)

(52) U.S. Cl.
CPC ........... *C12N 1/06* (2013.01); *C12N 15/1003* (2013.01)

(58) Field of Classification Search
None
See application file for complete search history.

(56) References Cited

U.S. PATENT DOCUMENTS

2009/0286301 A1* 11/2009 Tao ........................ C12N 1/066
435/198

OTHER PUBLICATIONS

Wilson, Kate, "Preparation of Genomic DNA from Bacteria," Current Protocols in Molecular Biology, 1997, pp. 2.4.1-2.4.5.*
Hudlow et al., "Development of a rapid, 96-well alkaline based differential DNA extraction method for sexual assault evidence," Forensic Science International: Genetics, 2012, vol. 6, pp. 1-16.*
Baird, M. et al., "Allele Frequency Distribution of Two Highly Polymorphic DNA Sequences in Three Ethnic Groups and Its Application to the Determination of Paternity," *Am J Hum Genet*, 1986, 39:489-501.
Benschop, Corina C.G. et al., "Post-coital vaginal sampling with nylon flocked swabs improves DNA typing," *Forensic Science International: Genetics*, 2010, 4:115-121.
Burger, Joachim et al., "DNA preservation: a microsatellite-DNA study on ancient skeletal remains," *Electrophoresis*, 1999, 20:1722-1728.
Elliott, K. et al., "Use of laser microdissection greatly improves the recovery of DNA from sperm on microscope slides," *Forensic Science International*, 2003, 137:28-36.
Fondevila, M. et al., "Challenging DNA: Assessment of a range of genotyping approaches for highly degraded forensic samples," *Forensic Science International: Genetics Supplemental Series*, 2008, 1:26-28.
Gill, Peter et al., "Forensic application of DNA 'fingerprints'," *Nature*, Dec. 1985, 318(12):577-579.
Horsman, Katie M. et al., "Separation of Sperm and Epithelial Cells in a Microfabricated Device: Potential Application to Forensic Analysis of Sexual Assault Evidence," *Anal. Chem.*, 2005, 77:742-749.
Hudlow, William R. et al., "Development of a rapid, 96-well alkaline based differential DNA extraction method for sexual assault evidence," *Forensic Science International: Genetics*, 2012, 6:1-16.
Jeffreys, Alec J. et al., "Hypervariable 'minisatellite' regions in human DNA," *Nature*, Mar. 7, 1985, 314:67-73.
Johanisson, E. et al., "Evaluation of 'round cells' in semen analysis: a comparative study," *Human Reproduction Update*, 2000, 6(4):404-412.
Kirkman-Brown, Jackson et al., "Evaluation of a disposable plastic Neubauer counting chamber for semen analysis," *Fertility and Sterility*, Feb. 2009, 91(2):627-631.
Norris, Jessica V. et al., "Expedited, Chemically Enhanced Sperm Cell Recovery from Cotton Swabs for Rape Kit Analysis," *J Forensic Sci*, Jul. 2007, 52(4):800-805.
Pang, B.C.M. et al., "Double swab technique for collecting touched evidence," *Legal Medicine*, 2007, 9:181-184.
Raymond, Jennifer J. et al., "Trace evidence characteristics of DNA: A preliminary investigation of the persistence of DNA at crime scenes," *Forensic Science International: Genetics*, 2009, 4:26-33.
Smejkal, Gary B. et al., "Increased Protein Yields from *Escherichia coli* Using Pressure-Cycling Technology," *Journal of Biomolecular Techniques*, 2006, 17:173-175.

(Continued)

*Primary Examiner* — Young J Kim
(74) *Attorney, Agent, or Firm* — Saliwanchik, Lloyd & Eisenschenk (57) ABSTRACT

The subject invention provides a two-step protocol using pressure cycling technology (PCT) and alkaline lysis for differential extraction of mixtures. In a preferred embodiment the procedure is used in forensic DNA applications such as, for example, DNA testing in the case of rape.

14 Claims, 5 Drawing Sheets

(56) References Cited

OTHER PUBLICATIONS

Virkler, Kelly et al., "Analysis of body fluids for forensic purposes: From laboratory testing to non-destructive rapid confirmatory identification at a crime scene," *Forensic Science International*, 2009, 188:1-17.
Vuichard, Séverine et al., "Differential DNA extraction of challenging simulated sexual-assault samples: a Swiss collaborative study," *Investigative Genetics*, 2011, 2(11):1-7.
Wiegand, P. et al., "DNA extraction from mixtures of body fluid using mild preferential lysis," *Int J Leg Med*, 1992, 104:359-360.
Wickenheiser, Ray A. et al., "Trace DNA: A Review, Discussion of Theory, and Application of the Transfer of Trace Quantities of DNA Through Skin Contact," *Journal of Forensic Sciences*, Mar. 2003, 48(2):1-11.
Yoshida, Kanako et al., "The modified method of two-step differential extraction of sperm and vaginal epithelial cell DNA from vaginal fluid mixed with semen," *Forensic Science International*, 1995, 72:25-33.
Schoell, Wolfgang M. J. et al., "Separation of Sperm and Vaginal Cells Based on Ploidy, MHC Class I-, CD45-, and Cytokeratin Expression for Enhancement of DNA Typing After Sexual Assault," *Cytometry*, 1999, 36:319-323.
Schoell, Wolfgang M. J. et al., "Separation of Sperm and Vaginal Cells with Flow Cytometry for DNA Typing After Sexual Assault," *Obstetrics & Gynecology*, Oct. 1999, 94(4):623-627.
Voorhees, Jessica C. et al., "Enhanced Elution of Sperm from Cotton Swabs Via Enzymatic Digestion for Rape Kit Analysis," *J Forensic Sci.*, May 2006, 51(3):574-579.

\* cited by examiner

MATERIALS AND METHODS FOR ACHIEVING DIFFERENTIAL LYSIS OF MIXTURES WITH THE AID OF ALKALINE LYSIS AND PRESSURE CYCLING TECHNOLOGY (PCT)

CROSS-REFERENCE TO A RELATED APPLICATION

This application claims the benefit of U.S. provisional application Ser. No. 61/941,201, filed Feb. 18, 2014, which is incorporated herein by reference in its entirety.

This invention was made with government support under contract number 2011-ne-bx-k550 awarded by the National Institutes of Justice. The government has certain rights in the invention.

BACKGROUND OF THE INVENTION

Since its discovery in 1984 by Sir Alec Jeffreys [9], DNA fingerprinting has become an indispensable tool in applications ranging from paternity testing [1], criminal investigations [12], to the study of genetic disorders [9]. The application of DNA technology in the criminal justice system has resulted in an unprecedented expansion in the capabilities of forensic laboratories for the detection of violent crimes such as rape and murder. With improvements in automation, the procedure has expanded to permit determination of property crimes and misdemeanors as well. However, as the number of applications for DNA technology has expanded, inevitable backlogs have occurred due to increasing sample loads. Factors such as time lapse between the incident and sample recovery [10], exposure to external elements [3, 5], and storage conditions, may all result in sample degradation. Hence it is critical to be able to efficiently recover and reliably analyze the evidence collected.

Traditionally, cotton swabs have been used for collection of biological samples such as body fluids, touch samples, and other trace evidence. Despite being a common tool for sample collection, sample extraction from these swabs can be challenging due to strong adherence of the sample to the matrix. Often the bulk of a collected biological sample remains entrapped in the cotton fibers even after elution. This results in a loss of precious evidence [14]. For sexual assault casework in which there is a mixture of body fluids present, there are two challenges. First, the evidence is often overwhelmed with the victim's vaginal epithelial cells and secondly the poor recovery from the swab can often make it difficult to recover the suspect male DNA profile [14, 19].

There have been a number of studies to develop methods to increase the efficiency of cell recovery from cotton swabs. Enzymatic methods are based on the hypothesis that upon digestion of cotton fibers with cellulase enzyme will improve the release of cells from the swab [19]. Alternatively, appropriate detergents or buffers may improve recovery of DNA from the cotton swabs [14]. Different types of swabs and substrates have also been proposed to improve elution of DNA [2].

Another issue is the selectivity of the extraction of DNA. When performing differential extraction of sperm and epithelial cells, it is critical to obtain a clean, unambiguous male profile. This is done by lysing the female epithelial cells with detergent followed by wash steps to isolate the sperm cells. This step is followed by treatment of the sperm cells with detergent and a reducing agent such as dithiothreitol to lyse disulfide bonds in sperm protamine and release the DNA. [6]. Because the procedure is difficult and time consuming, involving multiple wash steps, its recovery is sometimes very poor and user dependent [20]. For example, in a collaborative study by Vuichard, it was found that losses up to 98% of the male DNA were seen in a standard differential extraction and in 30% of these extractions more male DNA was found in the epithelial fraction than the sperm fraction [20].

Because of these problems, a number of alternative procedures have been attempted to permit differential detection of male and female DNA. These include laser microdissection[4], removal of female DNA through alkaline lysis and DNase digestion[8], microfluidics [7] and flow cytometry [16, 17].

Although there have been a number of efforts to improve either the recovery or the extraction of DNA from swabs taken following a sexual assault, the ability to achieve both would be desirable, especially for situations in which sample is limited. Though the organic differential extraction method developed by Gill et al. is still a gold standard in analyzing mixtures [21, 23], its shortcomings create the need for an efficient, quick, and reliable method that can successfully separate DNA profiles in a mixture without compromising sample recovery.

BRIEF SUMMARY

The subject invention provides a two-step protocol using pressure cycling technology (PCT) and alkaline lysis for differential extraction of mixtures. In a preferred embodiment the procedure is used in forensic DNA applications such as, for example, DNA testing in the case of rape.

In accordance with the subject invention, it was found that, for mixtures of sperm and female epithelial cells, pressure treatment in the presence of alkaline conditions resulted in a near complete recovery of female epithelial DNA. Following this pressure treatment, exposing the composition to alkaline conditions at higher temperatures results in selective recovery of sperm DNA with minimal contamination from female epithelial cells.

In one embodiment, the selective recovery of sperm DNA was optimized by examining the effect of sodium hydroxide concentration, incubation temperature and time. 69±6% of sperm DNA was recovered from prepared mixtures in the presence of 0.4 N NaOH at 95° C. for 5 minutes. Following alkaline lysis, the samples were neutralized with 2 M Tris (pH 7.5) and purified with phenol-chloroform-isoamyl alcohol to permit downstream analysis. The total processing time to remove both fractions from the swab was less than 30 minutes. Short tandem repeat (STR) analysis of these fractions obtained from PCT treatment and alkaline lysis generated clean profiles of female epithelial DNA and male sperm DNA, respectively.

By reducing the time for the recovery of DNA from sexual assault mixtures, this new method improves the efficiency of current differential extraction techniques, aiding in effective processing of forensic casework.

DETAILED DISCLOSURE

In a sexual assault case, sample is collected from the victim, often female, due to which the sperm sample from a male offender is overwhelmed with the presence of female vaginal epithelial cells. To obtain a clean male genetic profile that will aid in identifying the suspect, it is imperative to separate these two cell fractions without losing evidentiary material. In accordance with the subject invention, pressure cycling technology (PCT) is utilized in conjunction with optimized alkaline conditions to selectively lyse female epithelial cells. Subsequently, exposing the sample to a higher temperature and a short incubation time in the presence of alkaline conditions produced lysis of sperm cells. The amalgamation of these two methods in a sequential manner results in the fast and efficient separation of female and male fractions from a mixture.

Pressure Cycling Technology (PCT) uses, for example, Barocycler® NEP 2320, a commercially available instrument from Pressure BioSciences Inc. (South Easton, Mass.), equipped with a hydrostatic pressure chamber that generates alternating cycles of ambient and high pressures with a range of 5-45 kpsi. Samples such as cotton swabs or cuttings of cloth can be directly extracted using this technique by simply placing them in a PULSE™ tube, a specially designed tube to withstand high pressures, along with an appropriate buffer.

Different PCT parameters such as pressure and number of cycles were tested to obtain optimum recoveries and selective extraction of a single cell type. For alkaline conditions, commercially available sodium hydroxide crystals were dissolved in HPLC grade water in concentrations ranging from 0.2N NaOH to 1.0 N NaOH to determine the effect of alkalinity on lysis of sperm cells and epithelial cells. Other bases can also be used. Apart from this, the effect of temperature and incubation time at different temperatures, under varying concentrations of sodium hydroxide was also studied to determine the optimal parameters for differential lysis. After studying all the individual parameters, a two-step protocol that results in separation of female epithelial DNA and male sperm DNA from mixtures was developed.

In the first step of one embodiment of the process of the subject invention, the swab containing the mixture was transferred to a PULSE™ tube containing 0.4N NaOH and was subjected to 20,000 psi pressure for 10 cycles. After pressure treatment, the swab was transferred to a 1.5 mL microcentrifuge tube and the remaining solution in the PULSE™ tube was subjected to phenol chloroform isoamyl alcohol (PCIA) purification to remove cellular debris and purify DNA for downstream analysis. In the second step, 0.4N NaOH was added to the swab from step one and incubated at 95° C. for 5 minutes in a water bath. Following incubation, the swab was transferred to a spin basket and centrifuged at 13000 rpm for 5 minutes and the DNA from the eluate was recovered with PCIA purification.

Different pressure parameters such as amount of pressure, time and number of cycles have been studied to determine the optimum conditions to achieve epithelial cell lysis in the presence of sodium hydroxide.

The method was successfully tested on simulated samples to address two major hurdles that have caused the bottleneck in DNA analysis of sexual assault samples. First and foremost, the extraction procedure is very fast and can be achieved in 10 minutes and secondly, significant amounts of DNA were recovered from cotton swabs compared to the current methods. Cotton swabs have been known to be a difficult matrix to work with considering the challenges associated with successfully recovering sample from tightly wound fibers. Advantageously, the method of the subject invention uses inexpensive buffers, has a very short extraction time, and importantly, can recover most of the DNA from the matrix, which is a significant improvement to the methods in existence.

The initial results obtained during optimization of pressure parameters demonstrated the potential of PCT in differential extraction with liquified samples but the DNA recoveries dropped when the study was repeated with cotton swabs. Since cotton swabs are commonly used for evidence collection in a crime scene, our efforts were focused on improving recoveries from a swab while maintaining selectivity at the same time. The role of temperature and many buffer compositions, including detergents, cellulase enzyme and reducing agents were studied in the process to determine their effect on cell recovery from a swab. By varying pressure and number of cycles, it was observed that at 20,000 psi at 10-20 cycles, epithelial cells were completely lysed with minimal lysis of sperm cells. Initial studies on alkaline lysis indicated that more than 70% of sperm DNA was recovered at high temperatures in the presence of sodium hydroxide. In one embodiment, the swab from PCT treatment is incubated at 95° C. for 5 minutes. The fractions from PCT treatment and alkaline lysis can be further purified with phenol chloroform isoamyl alcohol (PCIA), or equivalent, to purify DNA for downstream analysis. A comparison of the genotypes of the purified fractions with sperm and epithelial controls indicated that this method successfully separated male and female fractions from mixture.

The procedure of the subject invention improves the speed and reliability of differential extraction, by eliminating the need for long incubation and digestion times as well as reducing the number of manual wash steps. Advantageously, the method of the subject invention does not require DNase.

In accordance with the subject invention, when there is a comparable amount of female epithelial cells and male sperm cells present in the sample, it is possible to generate a clean male DNA profile with a ten-minute extraction involving pressure cycling technology and alkaline lysis. In the presence of overwhelming amount of epithelial cells, it is necessary to increase the digestion time to minimize the contamination of sperm fraction.

With a total of time of 20 minutes to remove both sperm and epithelial cells from spiked swabs, this new process is quick and efficient. Current methods for removal of cellular debris from swabs require an incubation time of 2-4 hours, which does not include the differential DNA extraction. By using sodium hydroxide solution for lysis and phenol-chloroform-isoamyl alcohol to purify the extracted sample, it is now possible to use simple solvents available in every lab, to rapidly, efficiently and accurately separate sperm and epithelial fractions. This gives leeway to substitute different methods for downstream purification to further streamline the process that is suited to individual labs.

Although the method of the subject invention has been exemplified herein primarily in the context of the analysis of a rape kit, the skilled artisan having the benefit of this disclosure would appreciate that the method can be used in a variety of settings and a variety of biological samples wherein DNA is to be separated from cells and/or other biological materials.

Materials and Methods

Sample Preparation

Vaginal epithelial cells and semen samples were collected from volunteers in accordance with protocols approved by the Institutional Review Board (IRB) of Florida International University. The samples were suspended in 1×PBS buffer (pH 7.4) (Fisher Scientific, NJ) and diluted to approximately 1 million cells per milliliter. The cell count was performed using a disposable hemocytometer (INCYTO C-Chip, Covington, Ga., USA) [13]. Equal volume of epithelial cells and sperm cells were added to a cotton swab and air dried at room temperature. Post-coital samples obtained from healthy volunteers were stored at −20° C. until further use.

The total amount of DNA in a known volume of sample was determined by extracting the samples using stain extraction buffer (10 mM Tris, 100 mM NaCl, 10 mM EDTA, 2% SDS, 39 mM DTT) and proteinase K (20 mg/ml) digestion. In order to determine the recovery efficiencies, the amount of DNA recovered from subsequent experiments during method development was calculated as percent recovery compared to DNA extracted from neat sperm sample or neat epithelial samples using organic extraction.

DNA Extraction

Alkaline Lysis

Hudlow et al. developed an alkaline-based differential extraction method that when combined with DNase digestion generated a purified sperm fraction as determined by STR genotyping [8]. Upon applying this method and quantifying the extracted DNA, it was observed that there was a significant loss of sperm DNA prior to DNase digestion. This led us to initiate a study to determine the effect of alkaline lysis on sperm cells and vaginal epithelial cells without DNase digestion at different temperatures and concentrations of sodium hydroxide.

Sodium hydroxide crystals (Fisher Scientific, NJ) were dissolved in molecular biology grade water (Fisher Scientific, NJ) to achieve concentrations of 0.2 N, 0.4 N, 0.6 N, 0.8 N and 1 N NaOH. In order to maximize DNA recovery from cotton swabs, three different incubation temperatures (75°, 85°, and 95° C.) and two different incubation times (2 minutes and 5 minutes) were studied for each concentration of sodium hydroxide solution. A cotton swab containing equal volume of sperm cells and epithelial cells was suspended in 400 μL of a specific concentration of sodium hydroxide solution and exposed to either 75°, 85°, or 95° C. for 2 or 5 minutes.

Pressure Cycling Technology (PCT)

A Barocycler® NEP 2320 (Pressure BioSciences Inc., South Easton, Mass.) was used to generate cycles of high pressure and ambient pressure to apply mechanical stress on the cells and cause lysis [18]. After determining the effect of alkaline conditions on sperm cells and epithelial cells, different pressure parameters such as amount of pressure and number of cycles were studied to achieve selectivity in extraction. PULSE™ tubes are specially designed tubes that are able to withstand high pressures. To perform pressurized extraction, a swab containing a mixture of sperm cells and vaginal epithelial cells was transferred to a PULSE™ tube containing 0.4 N NaOH solution (the optimum concentration determined by alkaline lysis studies) and exposed to 10000 psi, 20000 psi or 45000 psi to determine the optimal pressure to achieve selectivity in lysis. The efficiency of the pressure treatment in the presence of increasing number of cycles was studied by varying the cycle number between 10, 20 and 60. During each pressure cycle, the holding time of sample at ambient pressure (T1) and target pressure (T2) was 15 seconds each.

Post-Extraction Purification

Following extraction, the samples were neutralized with 2M Tris (pH 7.5). Then the swabs were transferred to DNA IQ™ Spin Baskets (Promega Corp., Madison, Wis.) and centrifuged at 13000 rpm for 5 minutes. Extracted samples were purified by adding an equal volume of phenol-chloroform-isoamyl alcohol (25:24:1) (Sigma-Aldrich, St. Louis, Mo.) and precipitated with 3 M sodium acetate and 95% ethanol. Following precipitation, the pellet was washed with 70% ethanol, air-dried and re-suspended in 1× Tris-EDTA buffer (pH 8.0) (Fisher Scientific, NJ).

Quantification

The extracted DNA was quantified using real-time PCR assay with a commercially available kit, the Plexor® HY system (Promega Corp., Madison, Wis.) on Rotor-Gene 6000 (Corbett, Australia). The system can simultaneously quantify autosomal DNA and male DNA. By calculating the Autosomal/Y ratio, the amount of male DNA and female DNA recovered from the mixture could be determined. The percent recovery of each cell type was determined by comparing the resultant quantity of DNA with samples containing a single cell type that have been directly extracted with proteinase K (20 mg/mL) based organic extraction. All the samples were analyzed in triplicate and the Plexor® HY analysis was performed following the manufacturer's instructions (Plexor® HY system, Technical Manual# TM299, Promega Corp., Madison, Wis.).

Short Tandem Repeat (STR) Analysis

The quality of the DNA recovered from alkaline lysis and pressure treatment was assessed by performing STR analysis using PowerPlex® 16 HS system (Promega Corp., Madison, Wis.) according to manufacturer's protocols (PowerPlex® 16 HS system, Technical Manual# TMD022, Promega Corp., Madison, Wis.). Samples were amplified using GeneAmp® 9700 thermal cyclers and amplification products were separated using ABI Prism™ 310 genetic analyzer (Applied Biosystems, Foster City, Calif.). Data analysis was performed using GeneMapper® ID v3.2 (Applied Biosystems, Foster City, Calif.).

Following are examples that illustrate embodiments and procedures for practicing the invention. These examples should not be construed as limiting.

Example 1—Effect of Alkaline Lysis on DNA Recovery from Swab

The goal of the alkaline lysis studies was to determine parameters to maximize sperm DNA recovery from a cotton swab while maintaining sufficient selectivity to enable differential lysis of mixtures. The effect of varying concentrations of NaOH at different temperatures and incubation times was studied, and it was observed that incubating the swab in 0.4 N NaOH at 95° C. for 5 minutes resulted in the recovery of 2.5 times more sperm DNA than epithelial DNA (Table 1). Moreover, depending on NaOH concentration and temperature, either sperm DNA or epithelial DNA exhibited relatively higher recoveries from mixtures.

Though cotton swabs have been traditionally used to collect evidentiary material, recovery of biological samples is poor from this matrix. Many methods have been reported previously to improve cell recovery from cotton swabs [19] but they involve 2-4 hours incubation time. In cases where there are mixtures present, all the cellular material must be eluted prior to the extraction step, before differential lysis can take place. Our initial results demonstrated that by incubating the swab at high temperature in alkaline conditions, almost all the cellular DNA can be removed from the substrate in as little as 10 minutes. Furthermore, differential extraction of epithelial and sperm cells can be performed directly off of the swab without prior elution, by adjusting the concentration of base and the incubation parameters.

Our results show that at any given temperature, maximum DNA recovery from sperm cells is produced at 0.4-0.6 N NaOH, whereas 0.2 N NaOH produces optimal recovery of epithelial DNA. The best selectivity and reproducibility for the removal of sperm cells from the swabs was achieved by increasing the incubation time to 5 minutes in the presence of 0.4 N NaOH. The removal of sperm was further improved by increasing the temperature to 95° C., with the result that 99.6±1% of the sperm DNA was recovered from controlled mixtures. Lower temperatures and lower concentrations of base were more conducive for the selective recovery of DNA from female epithelial cells. Overall results are shown in Table 1.

TABLE 1

Percentage of DNA recovered from mixtures in the presence of alkaline conditions at high temperatures

| Concentration of NaOH solution (N) | Incubation temperature (° C.) | Incubation time (Minutes) | Sperm DNA recovered (%) | Vaginal epithelial DNA recovered (%) |
|---|---|---|---|---|
| 0.2 | 95 | 2 | 60 ± 6.2 | 74.7 ± 12.2 |
| 0.2 | 95 | 5 | 97.6 ± 10.3 | 78.4 ± 20.6 |
| 0.4 | 95 | 2 | *131.4 ± 22.4 | 63.8 ± 18 |
| 0.4 | 95 | 5 | 99.6 ± 1 | 40.6 ± 2 |
| 0.6 | 95 | 2 | *114.9 ± 14.6 | 46.1 ± 3.5 |
| 0.6 | 95 | 5 | 63.5 ± 11.4 | 54.4 ± 7.8 |
| 0.8 | 95 | 2 | 93.7 ± 6.9 | 41.9 ± 5 |
| 0.8 | 95 | 5 | 51.8 ± 11.6 | 41.4 ± 2.8 |
| 1 | 95 | 2 | 71 ± 4 | 32.6 ± 0.7 |
| 1 | 95 | 5 | 49 ± 6.9 | 44.5 ± 5.2 |
| 0.2 | 85 | 2 | 44.3 ± 12.8 | 85.2 ± 14 |
| 0.2 | 85 | 5 | 70.2 ± 7.9 | 60.2 ± 4.3 |
| 0.4 | 85 | 2 | 85.9 ± 5.1 | 68 ± 16.8 |
| 0.4 | 85 | 5 | 74.5 ± 10.2 | 47.4 ± 8.8 |
| 0.6 | 85 | 2 | 74.5 ± 9.9 | 51.8 ± 9.9 |
| 0.6 | 85 | 5 | 66.3 ± 5.9 | 35.2 ± 3.4 |
| 0.8 | 85 | 2 | 54.5 ± 6.1 | 35.4 ± 8.6 |
| 0.8 | 85 | 5 | 61.8 ± 7.6 | 44.9 ± 5.1 |
| 1 | 85 | 2 | 81.2 ± 6.2 | 52.9 ± 17 |
| 1 | 85 | 5 | 54.1 ± 1.8 | 55.2 ± 8.8 |
| 0.2 | 75 | 2 | 32.9 ± 6.1 | 69 ± 7.4 |
| 0.2 | 75 | 5 | 39.6 ± 5.5 | 41.4 ± 3.3 |
| 0.4 | 75 | 2 | 60 ± 9 | 46.1 ± 6 |
| 0.4 | 75 | 5 | 56.9 ± 1.4 | 29.9 ± 8 |
| 0.6 | 75 | 2 | *113.3 ± 6.1 | 52.3 ± 20.7 |
| 0.6 | 75 | 5 | 86.7 ± 18.7 | 45.8 ± 5.6 |
| 0.8 | 75 | 2 | 83.1 ± 16.1 | 41.1 ± 15.6 |
| 0.8 | 75 | 5 | 63.5 ± 16.7 | 37.8 ± 2.9 |
| 1 | 75 | 2 | 62.4 ± 5.6 | 33.6 ± 9 |
| 1 | 75 | 5 | 61.2 ± 2.4 | 34.1 ± 1.8 |

Note:
DNA recovery indicates the relative amount of DNA extracted in the experimental procedure compared to that extracted from neat samples using the standard phenol chloroform isoamyl alcohol procedure and is expressed as the mean (n = 3) ± standard error Note:
Bold and underlined parameters represent the optimized alkaline conditions for selective sperm DNA recovery from mixtures.

Note:
Values with asterisk (*) indicate that more DNA was recovered with the experimental parameters compared to the organic extraction of a similar amount of neat semen sample.

Example 2—Optimization of Pct Parameters

Although the results from the alkaline lysis studies showed that 0.4 N NaOH at 95 degrees gave the best recovery and selectivity for sperm DNA from mixtures, there was still some DNA recovery from epithelial cell lysis resulting in a mixed profile. Therefore a pressure-based extraction step was introduced to completely remove epithelial cells prior to recovering the sperm DNA. In order to do this, it was important to determine the effect of pressure treatment on the recovery of epithelial DNA from swabs in the presence of 0.4 N NaOH.

Figure 1:
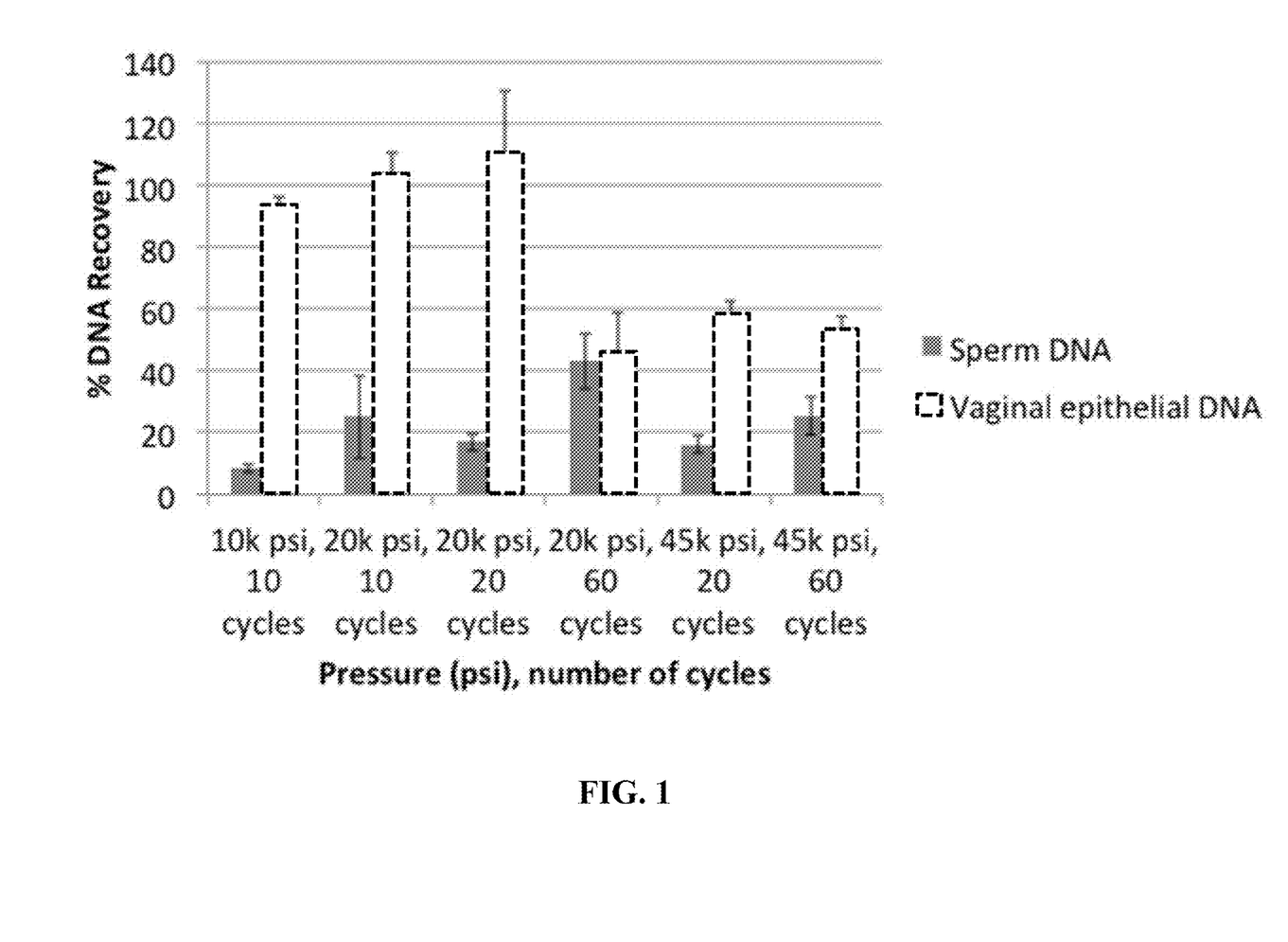
FIG. 1 illustrates the effect of pressure treatment on DNA recovery from mixtures in the presence of 0.4 N NaOH solution.

Our results indicated that 104±6% recovery of epithelial cells occurred at 20,000 psi using 10 cycles of pressure in the presence of 0.4 N NaOH (FIG. 1). Furthermore, this mild pressure treatment did not have a significant impact on sperm cell lysis thus enabling the development of a two-step differential extraction protocol. Another upside of this treatment was that compared to the current extraction methods which can take up to 2-4 hours to remove cells from a swab, the total time required to remove DNA from the swab using the pressure cycling procedure under alkaline conditions was just 10 minutes. Semen also contains non-spermatogenic cells such as epithelial and inflammatory cells that may be susceptible to digestion under same conditions as vaginal epithelial cells, therefore, the slight recovery of male DNA seen during PCT treatment may be due to the degradation of the non sperm cells present in semen [11].

Example 3—Development of a Two-Step Protocol for Differential Extraction

Figure 2:
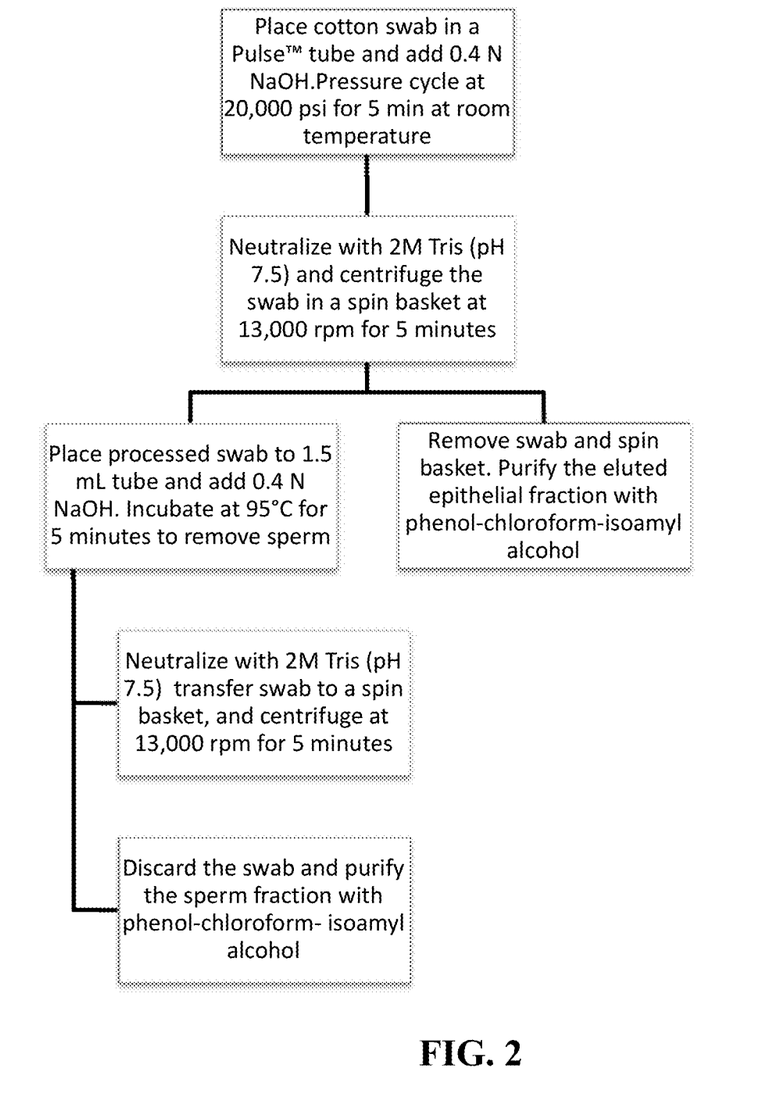
FIG. 2 is a flowchart depicting the protocol for differential extraction of mixtures using alkaline lysis and pressure cycling technology.

To achieve complete separation of both cell fractions and obtain a clean DNA profile, a two-step method was developed in which swabs were first placed in 0.4 N NaOH and exposed to pressure cycling for 5 min to remove the epithelial fraction. The cells remaining on the swab (sperm fraction) were then subjected to alkaline lysis at 95° C. for 5 min. To perform this process, the swab was first treated with 20,000 psi pressure for 10-20 cycles in the presence of 0.4 N NaOH solution. Following pressure treatment, the sample was immediately neutralized with 2 M Tris (pH 7.5) and the swab was transferred to a spin basket placed in 2.0 mL tube and centrifuged at 13,000 rpm for 5 minutes. DNA was purified with phenol-chloroform-isoamyl alcohol (25:24:1) followed by ethanol precipitation (epithelial fraction). The swab was transferred to a 1.5 mL tube containing 0.4 N NaOH solution and the sample (sperm fraction) was incubated at 95° C. for 5 minutes. Following incubation, the sample was neutralized with 2 M Tris (pH 7.5) and the swab was transferred to a spin basket for centrifugation at 13,000 rpm for 5 minutes. The swab was discarded, and DNA from the sperm fraction was purified using phenol-chloroform-isoamyl alcohol and ethanol precipitation (FIG. 2).

Figure 3A:
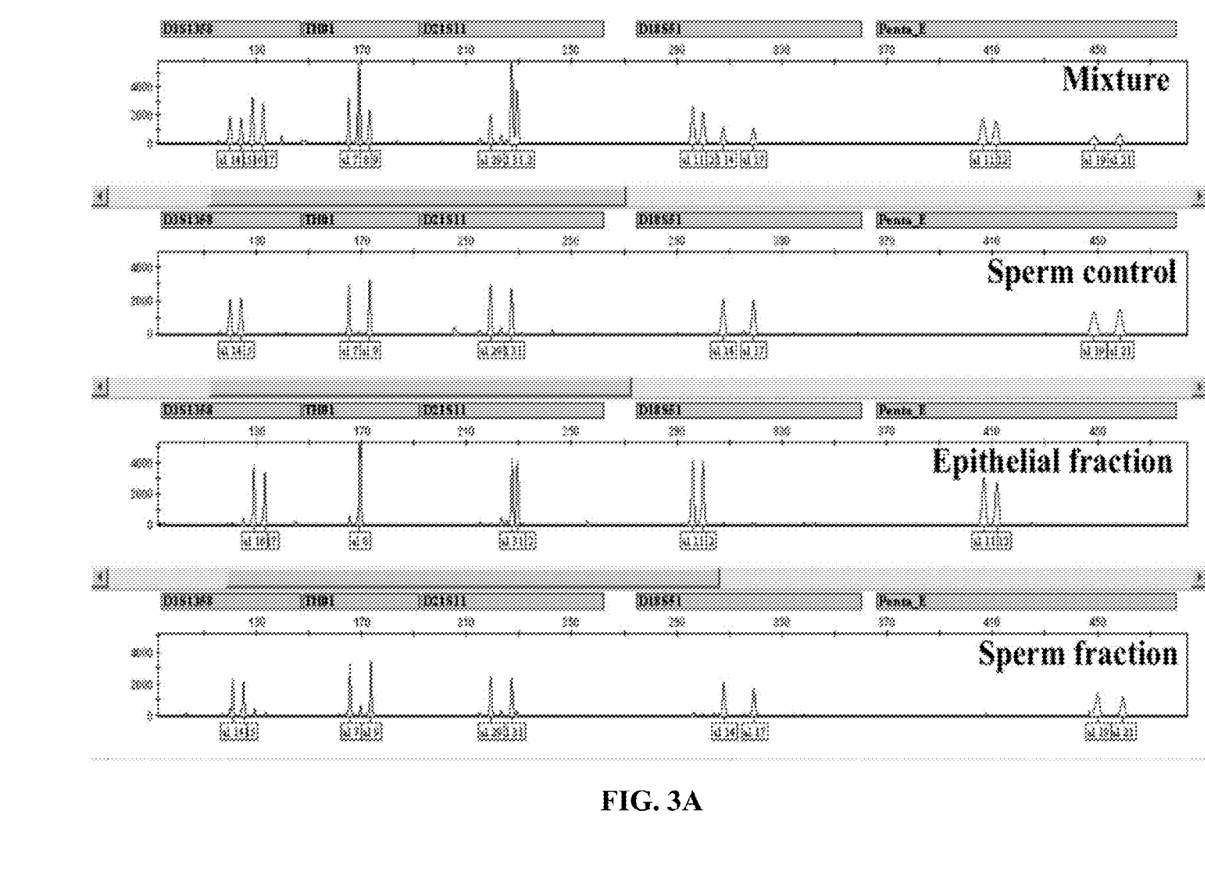
FIGS. 3A-3C illustrates Powerplex® 16 HS products of mixture, sperm control, epithelial fraction (post-PCT purified fraction) and sperm fraction (post-alkaline lysis treatment). (3A) Carboxy-tetramethylrhodamine (TMR) labeled loci (3B) Fluorescein (FL)-labeled loci (C) 6-carboxy-4',5'-dichloro-2',7'-dimethoxy-fluorescein (JOE)-labeled. Electropherogram shows that the DNA profile obtained from sperm fraction is identical to sperm control at all loci.
Figure 3B:
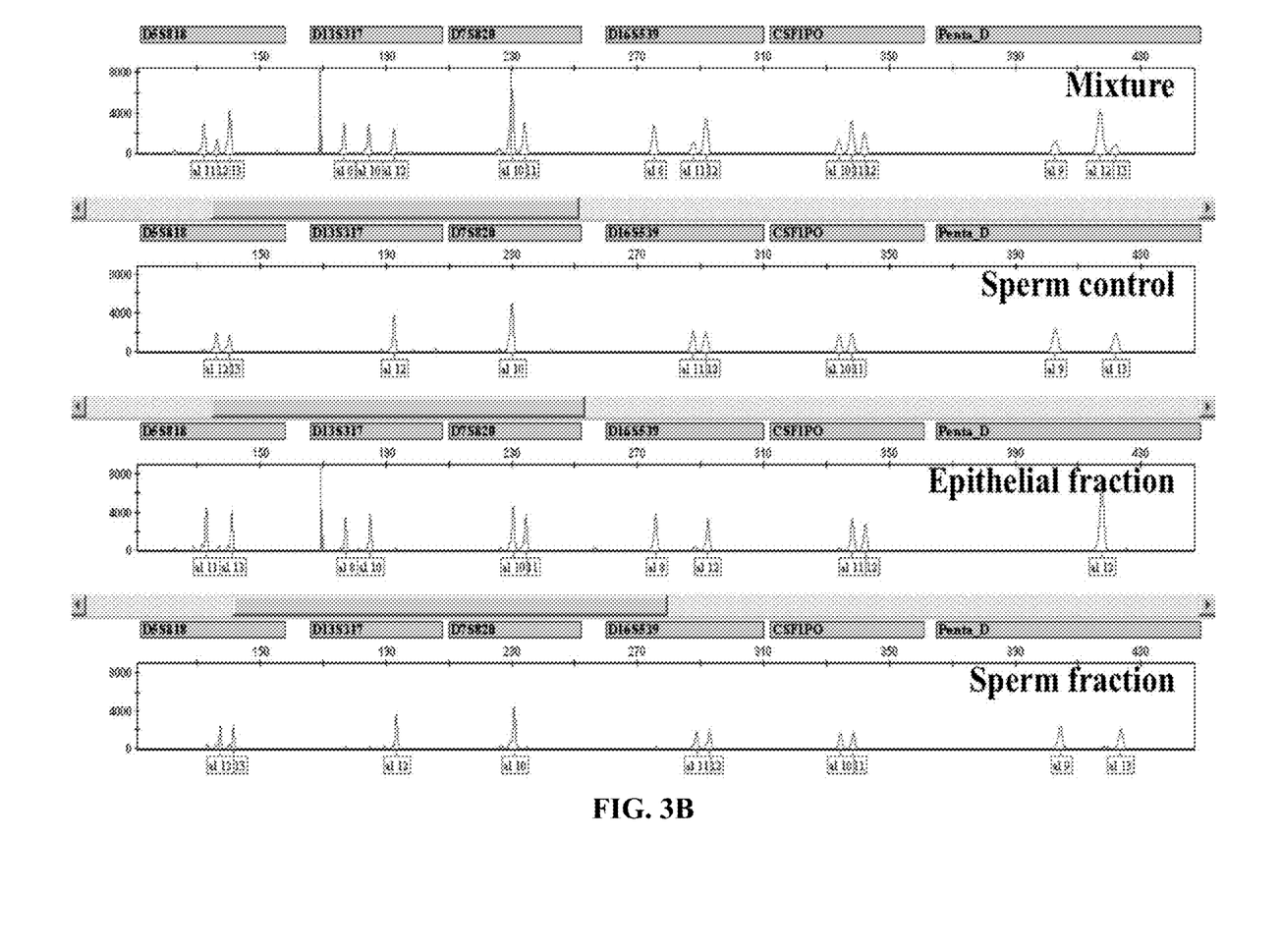
Figure 3C:
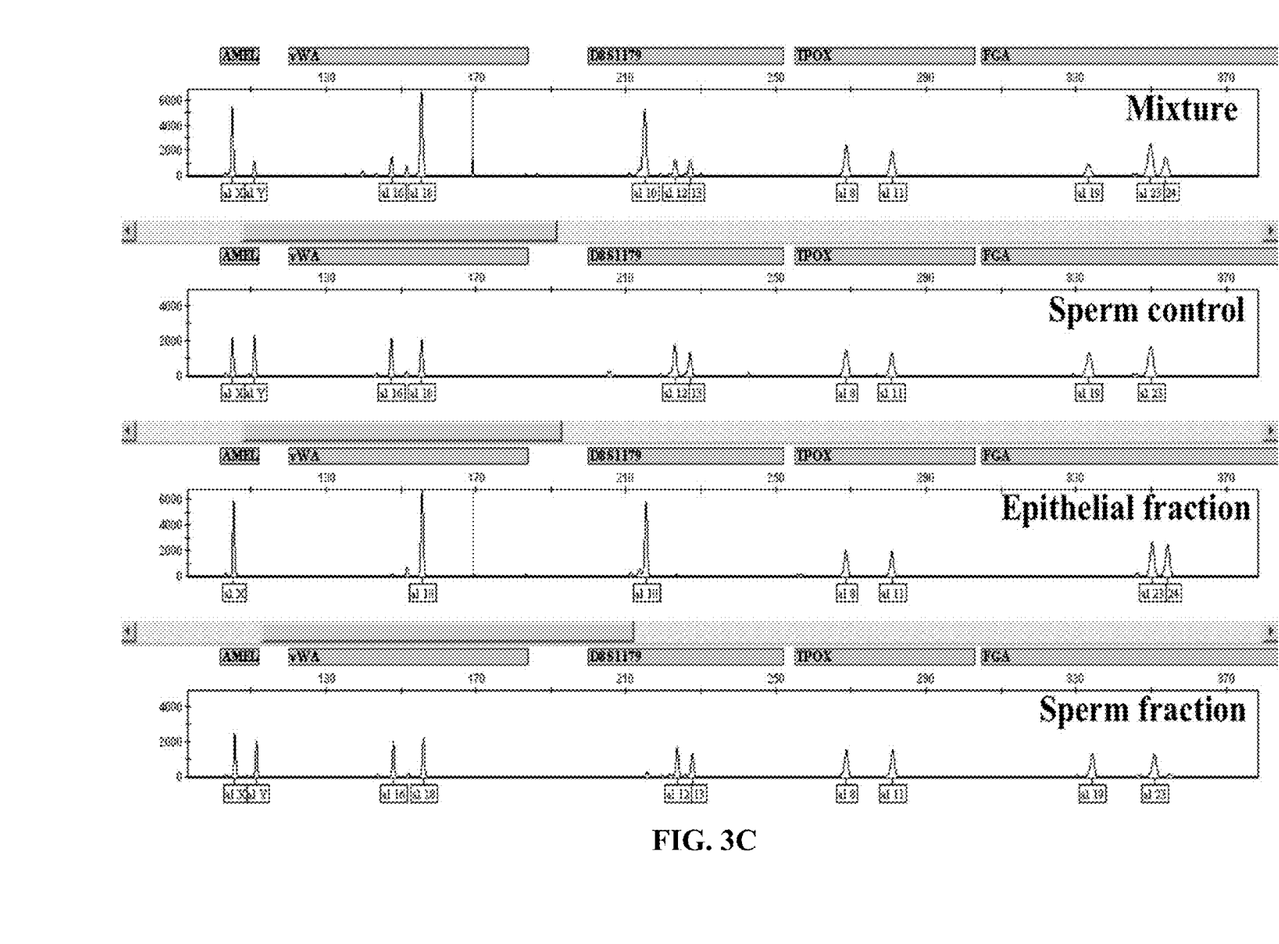

Short tandem repeat (STR) analysis of both epithelial and sperm fractions revealed that the male and female components were successfully separated from the mixture (FIG. 3). Comparative analysis of genotypes of mixture, neat sperm and epithelial samples with both the extracted fractions showed that this two-step protocol resulted in a clean male and female DNA profiles that are identical to the profiles generated with organic extraction of neat samples.

Example 4—Application of Alkaline Lysis-PCT Method to Post-Coital Samples

In order to determine whether this method can be a good alternative to analyze rape kits, we have applied it to post-coital vaginal swabs collected from female volunteers following different time intervals after sex. Multiple swabs were collected from each volunteer. From each volunteer, one swab was processed using the optimized experimental protocol and the second swab was processed with a validated standard differential extraction protocol used by Broward Sheriff's Office (BSO) crime lab. A comparative study was done to evaluate the ability of this method to separate mixtures in sexual assault samples. The ratio of autosomal to Y-chromosomal DNA concentrations was calculated using Plexor® HY software for epithelial and sperm fractions. A value closer to 1.0 indicates the ability to obtain a predominantly male autosomal STR profile whereas a higher value indicates the presence of more female alleles.

TABLE 2

A comparison of DNA recoveries and STR profiles of post-coital samples obtained with a validated extraction protocol to the results obtained with alkaline lysis and pressure cycling technology.

|  |  | Volunteer # 1 | Volunteer # 2 | Volunteer # 3 |
|---|---|---|---|---|
| Time lapse since intercourse |  | 0-5 hrs | 7-12 hrs | 13-18 hrs |
| BSO[a] method | [Auto]/[Y] in epithelial fraction[c] | 2.9 | 38 | 27 |
|  | [Auto]/[Y] in sperm fraction[c] | 0.5 | 0.8 | 1.0 |
| Alkaline lysis with pressure cycling[b] | [Auto]/[Y] in epithelial fraction[c] | 3.4 | 30 | 59.2 |
|  | [Auto]/[Y] in sperm fraction[c] | 0.6 | 46.4 | 2.4 |
| Ratio of X/Y alleles at Amelogenin locus: PP16 HS[d] (BSO method) |  | 1:1 [M] | 1:1 [M] | 1:1 [M] |
| Ratio of X/Y alleles at Amelogenin locus: PP16 HS[d] (Alkaline lysis + pressure cycling) |  | 1:1 [M] | No Male DNA Detected [F] | 5.4:1 [Mixture] |

[a]Differential extraction protocol used by Broward Sheriff's Office (BSO) crime lab is used for comparison with the current protocol in development.
[b]Alkaline lysis was used in conjunction with pressure cycling technology (PCT) to determine the ability of this method to analyze rape kits.
[c]Plexor ® HY system (Promega) was used to determine the ratio of autosomal to male (Y) DNA.
[d]PowerPlex ® 16 HS system (Promega) was used to generate DNA profile ((M = male DNA profile; M + F = mixed DNA profile; major = major component of the mixed DNA profile).

The results from alkaline lysis and pressure cycling of post-coital swabs obtained from volunteer #2 and volunteer #3 showed that when the ratio of autosomal to Y-chromosomal DNA concentrations in epithelial fraction exceeded 30, indicating an excess of female tissue, and the incomplete digestion of vaginal epithelial cells led to female DNA carryover into the sperm fraction. As a result, the autosomal to Y-DNA ratio of sperm fraction extracted from swab #2 indicated an overwhelming amount of female DNA, which is further evidenced by the presence of a single peak representing X amplicon at the Amelogenin locus. It should be noted that it is possible to reduce this carryover by exposing the swab to longer digestion times. Twice the amount of female DNA was present in the sperm fraction extracted from swab #3 as determined by the ratio of relative fluorescence units (RFU) in the X and Y sex typing alleles at Amelogenin locus. The autosomal to Y-DNA ratio of sperm fraction extracted from swab #1 is 0.6 and this indicates the presence of predominantly male alleles (Table 2). A clean male autosomal STR profile was obtained, which is identical to the sample extracted with the method used by Broward sheriff's office crime lab, and with much shorter processing time needed in comparison All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

[1]. Baird M., Balazs I., Giusti A., Miyazaki L., Nicholas L., Wexler K., Kanter E., Glassberg J., Allen F., Rubinstein P., Sussman L., *Am. J. Hum. Genet.* 1986, 39(4), 489-501.
[2]. Benschop C. C. G., Wiebosch D. C., Kloosterman A. D., Sijen T. *Forensic Sci. Int. Genet.* 2010, 4, 115-121.
[3]. Burger J., Hummel S., Herrmann B., Henke W., *Electrophoresis.* 1999, 20 (8), 1722-1728.
[4]. Elliot K., Hill D. S., Lambert C., Burroughes T. R., Gill P., *Forensic Sci. Int.* 2003, 137, 28-36.
[5]. Fondevila M., Phillips C., Naverán N., Cerezo M., Rodríguez A., Calvo R., Fernández L. M., Carracedo Á., Lareu M. V., *Forensic Sci. Int. Genet.* 2008, 1(1), 26-28.
[6]. Gill P., Jeffreys A. J., Werrett D. J., *Nature.* 1985, 318 (12), 577-579.
[7]. Horsman K. M., Barker S. L. R., Ferrance J. P., Forrest K. A., Koen K. A., Landers J. P., *Anal. Chem.* 2005, 77, 742-749.
[8]. Hudlow W. R., Buoncristiani M. R., *Forensic Sci. Int. Genet.* 2012, 6 (1), 1-16.
[9]. Jeffreys A. J., Wilson V., Thein S. W., *Nature.* 1984, 314, 67-73.
[10]. Jennifer J. R., Roland A. H. v. O, Peter R. G., Simon J. W., Claude R., *Forensic Sci. Int. Genet.* 2009, 4 (1), 26-33.
[11]. Johanisson E., Campana A., Luthi R., de Agostini A., *Hum. Reprod. Update.* 2000, 6 (4), 404-412.
[12]. Kelly V., Igor K. L., *Forensic Sci. Int.* 2009, 188 (1-3), 1-17.
[13]. Kirkman-Brown J., Björndahl L., *Fertil. Steril.* 2009; 91 (2), 627-31.
[14]. Norris J. V., Manning K., Linke S. J., Ferrance J. P., Landers J. P., *J. Forensic Sci.* 2007, 52 (4), 800-805.
[15]. Pang B. C. M., Cheung B. K. K., *Legal Med.* 2007, 9 (4), 181-184.
[16]. Schoell W. M., Klintschar M., Mirhashemi R., Pertl B., *Obstet. Gynecol.* 1999, 94 (4), 623-627.
[17]. Schoell W. M., Klintschar M., Mirhashemi R., Strunk D., Giuliani A., Bogensberger G., Pertl B., *Cytometry.* 1999, 36 (4), 319-23.
[18]. Smejkal G. B., Robinson M. H., Lawrence N. P., Tao F., Saravis C. A., Schumacher R. T., *J Biomol. Tech.* 2006, 17(2), 173-175.
[19]. Voorhees J. C., Ferrance J. P., Landers J. P., *J. Forensic Sci.* 2006, 51 (3), 574-579.
[20]. Vuichard S., Borer U., Bottinelli M., Cossu C., Malik N., Meier V., Gehrig C., Sulzer A, Morerod M., Castella V., *Investig Genet.* 2011, 2, 1.
[21]. Weigand P., Schurenkamp M., Schutte U., *Int. J. Legal Med.* 1992, 104(6), 359-60.
[22]. Wickenheiser R. A., *J. Forensic Sci.* 2002, 47 (3), 442-450.
[23]. Yoshida K., Sekiguchi K., Mizuno N., Kasai K., Sakai I., Sata H., Seta S., *Forensic Sci. Int.* 1995, 72, 25-33.

We claim:

1. A method of separating male sperm cells and female epithelial cells in a sample embedded in a cotton swab, comprising:
    immersing the sample in an alkaline solution comprising 0.2-0.8 N NaOH, wherein said alkaline solution does not comprise deoxyribonuclease (DNase);
applying pressure cycling technology (PCT) to the sample at room temperature, the PCT comprising the application of alternating cycles of ambient and high pressure to the sample, said high pressure being between 10,000 psi and 45,000 psi;
neutralizing the sample with a buffer solution;
centrifuging the sample to produce an eluted epithelial fraction;
collecting and purifying the eluted epithelial fraction for female DNA processing, whereby a sperm fraction is left in the cotton swab; and
processing the sperm fraction remaining in the cotton swab.

2. The method of claim 1, wherein the sample comprises the sperm and epithelial cells mixture embedded in a cotton swab collected from a forensic DNA test conducted in a rape case.

3. The method of claim 1, wherein the concentration of NaOH is 0.4 N.

4. The method of claim 1, wherein the high pressure is 20,000 psi.

5. The method of claim 4, wherein the number of alternating pressure cycles is at least 10 and not more than 60.

6. The method of claim 5, wherein the number of alternating pressure cycles is 10.

7. The method of claim 1, wherein the neutralizing buffer solution is tris(hydroxymethyl) aminomethane ("Tris"), said buffer solution having a pH of 7.5.

8. The method of claim 1, wherein the step of purifying the eluted epithelial fraction comprises:
    treating the elution with a solution comprising phenol, chloroform, and isoamyl alcohol (collectively PCIA) at a ratio of 25:24:1; and
    precipitating the epithelial cells into epithelial pellets using 3 M of sodium acetate and 95% ethanol; and
    suspending the epithelial pellets in 1X Tris-EDTA buffer havinga pH of 8.0.

9. The method of claim 1, wherein the step of processing the sperm fraction remaining in the cotton swab comprises:
    incubating the cotton swab embedded with the sperm fraction in an alkaline solution comprising 0.2-0.8 N NaOH;
    neutralizing the sperm fraction with a buffer solution comprising Tris at a pH of 7.5;
    centrifuging the sperm fraction to produce an eluted sperm fraction; and
    processing the eluted sperm fraction for male DNA.

10. The method of claim 9, wherein the incubation occurs at a temperature of at least 75° C. and not more than 95° C.

11. The method of claim 10, wherein the incubation temperature is 95° C.

12. The method of claim 9, wherein incubation occurs for a period of at least 2 minutes and not more than 5 minutes.

13. The method of claim 12, wherein the incubation period is 5 minutes.

14. The method of claim 9, wherein the step of processing the eluted sperm fraction comprises:
    treating the eluted sperm fraction with PCIA at a ratio of 25:24:1;
    precipitating the eluted sperm fraction into sperm pellets with 3 M of sodium acetate and 95% ethanol;
    washing the sperm pellets with 70% ethanol followed by air-drying; and
    suspending the sperm pellets in 1X Tris-EDTA buffer having a pH of 8.0.

* * * * *